United States Patent
Roh et al.

(10) Patent No.: US 12,415,778 B2
(45) Date of Patent: *Sep. 16, 2025

(54) METHOD FOR PREPARING PHTHALONITRILE-BASED COMPOUND

(71) Applicant: KOREA KUMHO PETROCHEMICAL CO., LTD., Seoul (KR)

(72) Inventors: Kee Yoon Roh, Daejeon (KR); Nam Hyun Cho, Daejeon (KR); Hee Su Kim, Daejeon (KR)

(73) Assignee: KOREA KUMHO PETROCHEMICAL CO., LTD., Seoul (KR)

( * ) Notice: Subject to any disclaimer, the term of this patent is extended or adjusted under 35 U.S.C. 154(b) by 611 days.

This patent is subject to a terminal disclaimer.

(21) Appl. No.: 17/940,576

(22) Filed: Sep. 8, 2022

(65) Prior Publication Data

US 2023/0096729 A1  Mar. 30, 2023

(30) Foreign Application Priority Data

Sep. 10, 2021 (KR) .................. 10-2021-0120763

(51) Int. Cl.
C07C 253/30 (2006.01)
C07C 253/34 (2006.01)

(52) U.S. Cl.
CPC .......... *C07C 253/30* (2013.01); *C07C 253/34* (2013.01)

(58) Field of Classification Search
CPC ... C07C 253/30; C07C 253/34; C07C 209/48; C07D 487/22; B01J 19/0006; B01J 19/0013
See application file for complete search history.

(56) References Cited

U.S. PATENT DOCUMENTS

2023/0096729 A1    3/2023  Roh et al.

FOREIGN PATENT DOCUMENTS

| CN | 107011211 B | 10/2018 |
| CN | 115135634 A | 9/2022 |
| EP | 4 148 039 A1 | 3/2023 |
| IN | 202247048769 A | 9/2022 |
| JP | 50-71643 A | 6/1975 |
| JP | 2023-515375 A | 4/2023 |
| KR | 10-2021-0098702 A | 8/2021 |
| RU | 2192411 C2 | 11/2002 |
| WO | 2022/092657 A1 | 5/2020 |
| WO | 2023/038411 A1 | 3/2023 |

OTHER PUBLICATIONS

Ahmed Adeyemi, et al., "Continuous Flow Synthesis under High Temperature/High Pressure Conditions using a Resistively Heated Flow Reactor", Organic Process Research & Development, Jun. 15, 2017, 1- 34 (35 pages).
David Cantrillo et al., "Direct Preparation of Nitriles from Carboxylic Acids in Continuous Flow", The Journal of Organic Chemistry, 2013, vol. 78, p. 10567-10571 (6 pages total).

*Primary Examiner* — Kamal A Saeed
*Assistant Examiner* — Quincy McKoy
(74) *Attorney, Agent, or Firm* — Sughrue Mion, PLLC

(57) ABSTRACT

An embodiment of the present invention provides a method for preparing a phthalonitrile-based compound, comprising: (a) feeding a mixture comprising a phthalic acid-based compound and a nitrile-based compound into a first reaction part to react; (b) transferring a resulting product of step (a) to a second reaction part connected to the first reaction part to react under the condition of 350 to 400° C.; and (c) obtaining a phthalonitrile-based compound at a discharge part connected to the second reaction part, wherein the second reaction part has a length in a fluid flow direction which is 10 times or more of a square root of an average cross-sectional area perpendicular to the fluid flow direction.

13 Claims, 1 Drawing Sheet

METHOD FOR PREPARING PHTHALONITRILE-BASED COMPOUND

TECHNICAL FIELD

The present specification relates to a method for preparing a phthalonitrile-based compound using a continuous process.

BACKGROUND ART

A phthalonitrile-based compound is an important compound used as an intermediate in the preparation of a fiber-forming linear polymer. Also, a phthalonitrile-based compound is used as an intermediate in the organic synthesize of various fine chemical products such as amines, acid amides, and composite nitrogen dyes, and is a high value-added raw material used for plasticizers, alkyd resin modifiers, insecticides, etc., as well.

Conventionally, a phthalonitrile-based compound was prepared by contacting a xylene compound with ammonia and an oxygen-containing gas in the presence of an oxidation catalyst and subjecting the same to dehydration reaction. Such methods, however, are an ammoxidation reaction that uses ammonia gas, a harmful chemical material, and is carried out in the presence of a catalyst at a high temperature and at a high pressure, of which the process is complicated, and should purify and separate high boiling point impurities through distillation, which makes it difficult to remove by-products. In addition, according to conventional methods for preparing a phthalonitrile-based compound, the yield of a product varies depending on the type of catalyst used in the ammoxidation reaction and the ratio of the oxygen-containing gas, and the conversion of the xylene compound, a precursor, is changed according to the reaction temperature, which makes it difficult to control the process.

Accordingly, there is a request for a process for preparing a phthalonitrile-based compound of high purity in an economic and environment-friendly manner.

DETAILED DESCRIPTION OF INVENTION

Technical Task

The present disclosure aims at solving the problems of the prior art described above. It is an object of the present disclosure to provide a method for preparing a phthalonitrile-based compound of high purity directly from a phthalic acid-based compound.

Means for Solving Technical Task

According to an aspect, a method for preparing a phthalonitrile-based compound, comprising: (a) feeding a mixture comprising a phthalic acid-based compound and a nitrile-based compound into a first reaction part to react; (b) transferring a resulting product of step (a) to a second reaction part connected to the first reaction part to react under the condition of 350 to 400° C.; and (c) obtaining a phthalonitrile-based compound at a discharge part connected to the second reaction part, wherein the second reaction part has a length in a fluid flow direction which is 10 times or more of a square root of an average cross-sectional area perpendicular to the fluid flow direction, is provided.

In an embodiment, the second reaction part may have a capacity of 1 to 50 parts by volume based on 100 parts by volume of the first reaction part.

In an embodiment, the phthalic acid-based compound may be isophthalic acid, terephthalic acid or a mixture thereof.

In an embodiment, the nitrile-based compound may be at least one selected from the group consisting of hydrogen cyanide, acetonitrile, acrylonitrile, butyronitrile, isobutyronitrile, pivalonitrile, succinonitrile, fumaronitrile, crotonitrile and benzonitrile.

In an embodiment, the mixture in step (a) may comprise a phthalic acid-based compound and a nitrile-based compound.

In an embodiment, in step (a), the nitrile-based compound may be contained in an amount of 1 to 500 parts by weight based on 1 part by weight of the phthalic acid-based compound.

In an embodiment, in step (a), the mixture may have a water content of less than 6,000 ppm.

In an embodiment, the reaction of step (a) may be performed under the conditions of 260 to 350° C. and 40 to 200 bar.

In an embodiment, in step (b), a flow rate of the resulting product of step (a) transferred to the second reaction part may be adjusted to 100 to 5,000 ml/min.

In an embodiment, in step (b), the resulting product of step (a) and the second reaction part may be in contact for 60 minutes or less.

In an embodiment, the reaction in step (b) may be performed under the condition of 40 to 200 bar.

In an embodiment, step (b) may be performed for 1 to 500 minutes.

In an embodiment, step (c) may perform separation and purification of the phthalonitrile-based compound from a product obtained at the discharge part.

In an embodiment, a residual compound separated in step (c) may be reused in step (a).

Effect of Invention

According to an aspect of the present specification, a phthalonitrile-based compound of high purity may be prepared directly from a phthalic acid-based compound in an environment-friendly manner.

Also, according to another aspect of the present specification, the amount of by-products produced is reduced and the reaction time is shortened, and thus a process for preparing a phthalonitrile-based compound from a phthalic acid-based compound may be performed more effectively.

The effects of an aspect of the present invention are not limited to the above-mentioned effects, and it should be understood that the effects of the present invention include all effects that could be inferred from the configuration of the invention described in the detailed description of the invention or the appended claims.

BEST MODE FOR CARRYING OUT THE INVENTION

Figure 1:
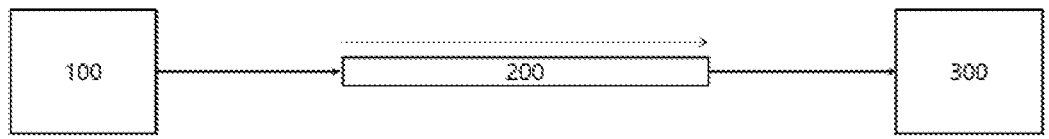
FIGS. 1 to 4 are schematic block diagrams illustrating a system for preparing a phthalonitrile-based compound used in an embodiment of the present disclosure.

Hereinafter, an aspect of the present specification will be described with reference to the accompanying drawings.

However, the description of the present specification may be implemented in various different forms, and thus is not limited to the embodiments described herein. Also, in order to clearly explain an aspect of the present specification in the drawings, portions that are not related to the present invention are omitted, and like reference numerals are used to refer to like elements throughout the specification.

Throughout the specification, it will be understood that when a portion is referred to as being "connected" to another portion, it can be "directly connected to" the other portion, or "indirectly connected to" the other portion having intervening portions present. Also, when a component "includes" an element, unless there is another opposite description thereto, it should be understood that the component does not exclude another element but may further include another element.

When a range of numerical values is described herein, the value has the precision of the significant figures provided according to the standard rules in chemistry for significant figures, unless a specific range thereof is stated otherwise. For example, 10 includes a range of 5.0 to 14.9 and the number 10.0 includes a range of 9.50 to 10.49.

Hereinafter, an embodiment of the present disclosure will be described in detail with respect to the accompanying drawings.

Method for Preparing Phthalonitrile-Based Compound

A method for preparing a phthalonitrile-based compound according to an aspect of the present specification may comprise: (a) feeding a mixture comprising a phthalic acid-based compound and a nitrile-based compound into a first reaction part 100 to react; (b) transferring a resulting product of step (a) to a second reaction part 200 connected to the first reaction part 100 to react under the condition of 350 to 400° C.; and (c) obtaining a phthalonitrile-based compound at a discharge part 300 connected to the second reaction part 200, wherein the second reaction part 200 has a length in a fluid flow direction which may be 10 times or more of a square root of an average cross-sectional area perpendicular to the fluid flow direction.

The method for preparing a phthalonitrile-based compound may be performed in a continuous process and, for example, may be performed using a system for preparing a phthalonitrile-based compound schematically shown in FIGS. 1 to 4, but is not limited thereto.

The system for preparing a phthalonitrile-based compound comprises a first reaction part 100; a second reaction part 200 connected to the first reaction part 100; and a discharge part 300 connected to the second reaction part 200, wherein in the second reaction part 200, a fluid flow may be present in the direction from the first reaction part 100 to the discharge part 300.

The first reaction part 100 may be a tank reactor, and may have a stirring means (not shown). The reaction of a phthalic acid-based compound and a nitrile-based compound may be first initiated and performed in the first reaction part 100.

The second reaction part 200 may be a type of tubular reactor wherein a length in a fluid flow direction has a value greater than that in a direction perpendicular to the fluid flow direction, and may have a stirring means (not shown). For example, the second reaction part may be a coil reactor, but is not limited thereto. FIGS. 1 to 4 use a straight line to indicate the second reaction part 200 and the fluid flow direction marked in a thin line, but are not limited thereto, and the second reaction part 200 and the fluid flow direction may be indicated as a curve such as a coil shape, as well as a straight line. In the second reaction part 200, the resulting product of step (a) may be additionally reacted, and part of by-products present in the resulting product of step (a) may be decomposed.

As used herein, a length of the second reaction part 200 refers to a distance through which a fluid flows from one end connected to the first reaction part 100 to the other end connected to the discharge part 300.

As used herein, a cross-sectional area of the second reaction part 200 refers to an area perpendicular to the fluid flow direction.

As used herein, "a square root of an average cross-sectional area" may refer to a value of a square root of a cross-sectional area if the cross-sectional area of the second reaction part 200 is unchangeable according to the location, or may be an $S_{sqrt}$ value calculated according to the following equation if the cross-sectional area of the second reaction part 200 is changeable according to the location:

$$S_{sqrt} = \frac{\int_0^L \sqrt{A(x)}\, dx}{L}, \quad \text{[Equation]}$$

wherein L is a length of the second reaction part 200, A(x) is a value of a cross-sectional area according to a point x from one end 0 connected to the first reaction part 100 to the other end L connected to the discharge part 300, and $S_{sqrt}$ is a value of a square root of the average cross-sectional area.

The second reaction part 200 may have a length that is 10 times or more of the square root of the average cross-sectional area. For example, the length may be 10 times, 15 times, 20 times, 25 times, 30 times, 35 times, 40 times, 45 times, 50 times, 55 times, 60 times, 65 times, 70 times, 75 times, 80 times, 85 times, 90 times, 95 times, 100 times, 105 times, 110 times, 115 times, 120 times, 125 times, 130 times, 135 times, 140 times, 145 times, 150 times, 155 times, 160 times, 165 times, 170 times, 175 times, 180 times, 185 times, 190 times, 195 times, 200 times, 205 times, 210 times, 215 times, 220 times, 225 times, 230 times, 235 times, 240 times, 245 times, 250 times, 255 times, 260 times, 265 times, 270 times, 275 times, 280 times, 285 times, 290 times, 295 times, 300 times, 305 times, 310 times, 315 times, 320 times, 325 times, 330 times, 335 times, 340 times, 345 times, 350 times, 355 times, 360 times, 365 times, 370 times, 375 times, 380 times, 385 times, 390 times, 395 times, 400 times, 405 times, 410 times, 415 times, 420 times, 425 times, 430 times, 435 times, 440 times, 445 times, 450 times, 455 times, 460 times, 465 times, 470 times, 475 times, 480 times, 485 times, 490 times, 495 times, 500 times, 505 times, 510 times, 515 times, 520 times, 525 times, 530 times, 535 times, 540 times, 545 times, 550 times, 555 times, 560 times, 565 times, 570 times, 575 times, 580 times, 585 times, 590 times, 595 times, 600 times, 605 times, 610 times, 615 times, 620 times, 625 times, 630 times, 635 times, 640 times, 645 times, 650 times, 655 times, 660 times, 665 times, 670 times, 675 times, 680 times, 685 times, 690 times, 695 times, 700 times, 715 times, 720 times, 725 times, 730 times, 735 times, 740 times, 745 times, 750 times, 755 times, 760 times, 765 times, 770 times, 775 times, 780 times, 785 times, 790 times, 795 times, 800 times, 805 times, 810 times, 815 times, 820 times, 825 times, 830 times, 835 times, 840 times, 845 times, 850 times, 855 times, 860 times, 865 times, 870 times, 875 times, 880 times, 885 times, 890 times, 895 times, 900 times, 905 times, 910 times, 915 times, 920 times, 925 times, 930 times, 935 times, 940 times, 945 times, 950 times, 955 times, 960 times, 965 times, 970 times, 975 times, 980 times, 985 times, 990 times, 995 times, 1,000 times, a range between any two of these values, or 1,000 times or more, for example, 10 to 1,000 times, but is not limited thereto. When the length of the second reaction part 200 deviates from the above range, the change control of the reaction temperature and/or reaction pressure is not sufficient, leading to degradation of the purify of a product, or an undue amount of time is required for the process, leading to decrease in productivity.

The second reaction part 200 may have a capacity of 1 to 50 parts by volume based on 100 parts by volume of the first reaction part 100. For example, the capacity may be 1 part by volume, 5 parts by volume, 10 parts by volume, 15 parts by volume, 20 parts by volume, 25 parts by volume, 30 parts by volume, 35 parts by volume, 40 parts by volume, 45 parts by volume, 50 parts by volume, or a range between any two of these values, but is not limited thereto. When the capacity of the second reaction part 200 is excessively larger than that of the first reaction part 100, the process efficiency may deteriorate, and when the capacity is excessively smaller, the effect of increasing the purity of a product may not be sufficient due to the control of reaction conditions.

FIG. 1 schematically illustrates a system for preparing a phthalonitrile-based compound. A second reaction part 200, a tubular reactor, is connected to a first reaction part 100, a tank reactor, to perform a reaction, and a product is obtained at a discharge part 300. Thereby, a problem of reducing the purity of a product due to a change in the reaction temperature and/or reaction pressure may be improved. The first reaction part 100 and second reaction part 200 use a valve (not shown) such as a flowmeter to adjust the input amount (flow rate) of the resulting product of step (a) transferred to the second reaction part 200.

Figure 2:
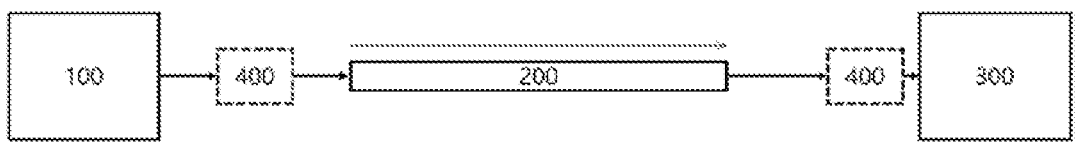

Referring to FIG. 2 that is another example of the system for preparing a phthalonitrile-based compound, the system may further comprise a pressure control part 400 between the first reaction part 100 and second reaction part 200 and/or between the second reaction part 200 and discharge part 300. When further comprising the pressure control part 400, the system may control the reaction pressure more precisely.

Figure 3:
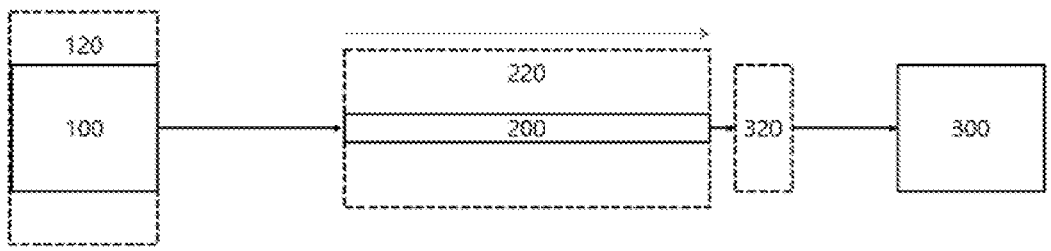

Referring to FIG. 3 that is another example of the system for preparing a phthalonitrile-based compound, at least one of the first reaction part 100, second reaction part 200 and discharge part 300 may further comprise a temperature control part 120, 220, 320. The temperature control part 120, 220 of the first reaction part 100 or second reaction part 200 may encompass each reaction part 100, 200 to keep a high reaction temperature, and the temperature control part 320 of the discharge part 300 may be positioned in front of the discharge part 300 to be used to cool down the product, but they are not limited thereto.

Figure 4:
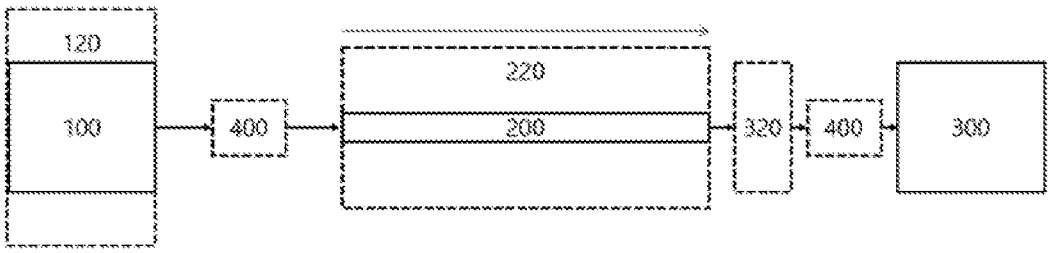

Referring to FIG. 4 that is another example of the system for preparing a phthalonitrile-based compound, the system may further comprise at least one of the temperature control parts 120, 220, 320 and at least one of the pressure control parts 400. The temperature control part 320 and pressure control part 400 may be interchangeably positioned.

With the system for preparing a phthalonitrile-based compound, the reaction temperature and pressure may be controlled more precisely, thereby obtaining a final product of high purity, and the total reaction time may be reduced, thereby achieving excellent productivity.

Step (a) is a step of feeding a reactant into the first reaction part 100 to react, and may be performed by feeding the mixture at room temperature, and then stirring the same for a predetermined time with the reaction temperature and reaction pressure set, but is not limited thereto.

The phthalic acid-based compound may be a compound having an aromatic ring and two or more carboxyl groups. For example, the phthalic acid-based compound may be isophthalic acid, terephthalic acid or a mixture thereof, but is not limited thereto.

The nitrile-based compound may be at least one selected from the group consisting of hydrogen cyanide, acetonitrile, acrylonitrile, butyronitrile, isobutyronitrile, pivalonitrile, succinonitrile, fumaronitrile, crotonitrile and benzonitrile, but is not limited thereto. The nitrile-based compound may be a reactant and also a solvent.

The method for preparing a phthalonitrile-based compound may perform a reaction without any additive such as ammonia, high concentration oxygen or a catalyst. Accordingly, the mixture of step (a) may consist of a phthalic acid-based compound and a nitrile-based compound, but is not limited thereto. For example, the mixture may be obtained by dissolving a phthalic acid-based compound in the solid phase in a nitrile-based compound solvent, but is not limited thereto.

In step (a), the nitrile-based compound may be contained in an amount of 1 to 500 parts by weight based on 1 part by weight of the phthalic acid-based compound. For example, based on 1 part by weight of the phthalic acid-based compound, the content of the nitrile-based compound may be 1 part by weight, 5 parts by weight, 10 parts by weight, 15 parts by weight, 20 parts by weight, 25 parts by weight, 30 parts by weight, 35 parts by weight, 40 parts by weight, 45 parts by weight, 50 parts by weight, 55 parts by weight, 60 parts by weight, 65 parts by weight, 70 parts by weight, 75 parts by weight, 80 parts by weight, 85 parts by weight, 90 parts by weight, 95 parts by weight, 100 parts by weight, 105 parts by weight, 110 parts by weight, 115 parts by weight, 120 parts by weight, 125 parts by weight, 130 parts by weight, 135 parts by weight, 145 parts by weight, 150 parts by weight, 155 parts by weight, 160 parts by weight, 165 parts by weight, 170 parts by weight, 175 parts by weight, 180 parts by weight, 185 parts by weight, 190 parts by weight, 195 parts by weight, 200 parts by weight, 205 parts by weight, 210 parts by weight, 215 parts by weight, 220 parts by weight, 225 parts by weight, 230 parts by weight, 235 parts by weight, 245 parts by weight, 250 parts by weight, 255 parts by weight, 260 parts by weight, 265 parts by weight, 270 parts by weight, 275 parts by weight, 280 parts by weight, 285 parts by weight, 290 parts by weight, 295 parts by weight, 300 parts by weight, 305 parts by weight, 310 parts by weight, 315 parts by weight, 320 parts by weight, 325 parts by weight, 330 parts by weight, 335 parts by weight, 345 parts by weight, 350 parts by weight, 355 parts by weight, 360 parts by weight, 365 parts by weight, 370 parts by weight, 375 parts by weight, 380 parts by weight, 385 parts by weight, 390 parts by weight, 395 parts by weight, 400 parts by weight, 405 parts by weight, 410 parts by weight, 415 parts by weight, 420 parts by weight, 425 parts by weight, 430 parts by weight, 435 parts by weight, 445 parts by weight, 450 parts by weight, 455 parts by weight, 460 parts by weight, 465 parts by weight, 470 parts by weight, 475 parts by weight, 480 parts by weight, 485 parts by weight, 490 parts by weight, 495 parts by weight, 500 parts by weight, or a range between any two of these values. As the content of the nitrile-based compound is greater compared to the content of the phthalic acid-based compound, the purity of a product may increase, but when the nitrile-based compound is contained in an excessive amount, it may be disadvantageous in terms of economic feasibility.

In step (a), the mixture may have a water content of less than 6,000 ppm. For example, the mixture may have a water content of less than 6,000 ppm, less than 5,000 ppm, less than 4,000 ppm, less than 3,000 ppm, less than 2,000 ppm, less than 1,000 ppm, less than 750 ppm, less than 500 ppm, or less than 250 ppm. As the mixture has lower moisture content, the purity of a product may increase.

In step (a), the reaction may be performed under the conditions of 260 to 350° C. and 40 to 200 bar. For example, the reaction may be performed at a reaction temperature of 260° C., 265° C., 270° C., 275° C., 280° C., 285° C., 290° C., 295° C., 300° C., 305° C., 310° C., 315° C., 320° C., 325° C., 330° C., 335° C., 340° C., 345° C., 350° C., or a range between any two of these values, and at a reaction pressure of 40 bar, 45 bar, 50 bar, 55 bar, 60 bar, 65 bar, 70 bar, 75 bar, 80 bar, 85 bar, 90 bar, 95 bar, 100 bar, 105 bar, 110 bar, 115 bar, 120 bar, 125 bar, 130 bar, 135 bar, 140 bar, 145 bar, 150 bar, 155 bar, 160 bar, 165 bar, 170 bar, 175 bar, 180 bar, 185 bar, 190 bar, 195 bar, 200 bar, or a range between any two of these values. When the reaction temperature of step (a) is excessively low, the purity of a product may decrease or no reaction may be performed, and when the reaction temperature is excessively high, the production of by-products may increase, which reduces the purity. When the reaction pressure of step (a) is excessively low, no reaction may be performed, and when the reaction pressure is excessively high, the stability may decrease.

In step (a), the reaction may be performed for 1 to 150 minutes. For example, the step (a) may be performed for 1 minute, 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, 120 minutes, 125 minutes, 130 minutes, 135 minutes, 145 minutes, or 150 minutes, and the duration may include a medium range of these values. When the reaction time of step (a) deviates from the above range, impurities may be formed, which reduces the purity, or the reaction may be insufficiently performed, which reduces the yield.

Step (b) is a step of transferring a resulting product of step (a) to the second reaction part 200 to react, and may be performed by setting the reaction temperature and reaction pressure of the second reaction part 200, and then transferring the resulting product of step (a) at a predetermined flow rate and stirring the same for a predetermined time to react, but is not limited thereto.

In step (b), a flow rate of the resulting product of step (a) transferred to the second reaction part 200 may be adjusted to 100 to 5,000 ml/min. For example, the flow rate may be 100 ml/min, 200 ml/min, 300 ml/min, 400 ml/min, 500 ml/min, 600 ml/min, 700 ml/min, 800 ml/min, 900 ml/min, 1,000 ml/min, 1,100 ml/min, 1,200 ml/min, 1,300 ml/min, 1,400 ml/min, 1,500 ml/min, 1,600 ml/min, 1,700 ml/min, 1,800 ml/min, 1,900 ml/min, 2,000 ml/min, 2,100 ml/min, 2,200 ml/min, 2,300 ml/min, 2,400 ml/min, 2,500 ml/min, 2,600 ml/min, 2,700 ml/min, 2,800 ml/min, 2,900 ml/min, 3,000 ml/min, 3,100 ml/min, 3,200 ml/min, 3,300 ml/min, 3,400 ml/min, 3,500 ml/min, 3,600 ml/min, 3,700 ml/min, 3,800 ml/min, 3,900 ml/min, 4,000 ml/min, 4,100 ml/min, 4,200 ml/min, 4,300 ml/min, 4,400 ml/min, 4,500 ml/min, 4,600 ml/min, 4,700 ml/min, 4,800 ml/min, 4,900 ml/min, 5,000 ml/min, or a range between any two of these values. When the flow rate is lower than the above range, the resulting product of step (a) and the second reaction part 200 are in contact for an excessively long time, which decreases the process efficiency, and the production of by-products may increase, which reduces the purity of a product. When the flow rate is higher than the above range, the contact time may be excessively short, which reduces the purity of a product. The flow rate may be adjusted using a mass flow controller (MFC), but is not limited thereto.

In step (b), the reaction may be performed under the condition of 350 to 400° C. For example, the reaction may be performed at a temperature of 350° C., 355° C., 360° C., 365° C., 370° C., 375° C., 380° C., 385° C., 390° C., 395° C., 400° C., or a range between any two of these values. When the reaction temperature of step (b) is lower than the above range, the purity of a product may be reduced or no reaction may be performed, and when the reaction temperature is excessively higher than the above range, the production of by-products may increase, which reduces the purity of a product.

The reaction temperature of step (b) may be higher than the reaction temperature of step (a). By setting the reaction temperature of the second reaction part 200 to 350 to 400° C. that is higher than the reaction temperature of the first reaction part 100, part of the by-products produced through the reaction of step (a) may be decomposed, and the decomposed by-products may react and be converted into a target product. Accordingly, a phthalonitrile-based compound of high purity with a reduced rate of the by-products may be prepared. In an embodiment, the decomposed by-products may be N-acetyl-3-cyano-benzamide (3-CBAA), but is not limited thereto.

In step (b), the resulting product of step (a) and the second reaction part 200 may be in contact for 60 minutes or less. For example, the contact time may be 60 minutes or less, 55 minutes or less, 50 minutes or less, 45 minutes or less, 40 minutes or less, 35 minutes or less, 30 minutes or less, 25 minutes or less, 20 minutes or less, 15 minutes or less, 10 minutes or less, 5 minutes or less, or 1 minute or less. When the contact time of the resulting product of step (a) and the second reaction part 200 satisfies the above range, part of the by-products produced through the reaction of step (a) is decomposed and converted into a target product, thereby increasing the purity of a product. When the contact time is longer than the above range, the production of by-products may increase, which reduces the purity of a product. The contact time may be controlled by adjusting at least one of the volume of the second reaction part 200, the flow rate of the resulting product of step (a) transferred to the second reaction part 200, the reactant per unit flow rate and the amount of a product discharged, but is not limited thereto. The contact time may refer to a residence time in the second reaction part 200.

In step (b), the reaction may be performed under the condition of 40 to 200 bar. For example, the reaction may be performed at a reaction pressure of 40 bar, 45 bar, 50 bar, 55 bar, 60 bar, 65 bar, 70 bar, 75 bar, 80 bar, 85 bar, 90 bar, 95 bar, 100 bar, 105 bar, 110 bar, 115 bar, 120 bar, 125 bar, 130 bar, 135 bar, 140 bar, 145 bar, 150 bar, 155 bar, 160 bar, 165 bar, 170 bar, 175 bar, 180 bar, 185 bar, 190 bar, 195 bar, 200 bar, or a range between any two of these values. When the reaction pressure of step (b) is excessively low, no reaction may be performed, and when the reaction pressure is excessively high, the stability may decrease. The reaction of step (b) may be performed under the same condition of a reaction pressure as the reaction of step (a), but is not limited thereto.

In step (b), the reaction may be performed for 1 to 500 minutes. For example, the step (b) may be performed for 1 minute, 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, 120 minutes, 125 minutes, 130 minutes, 135 minutes, 145 minutes or 150 minutes, 155 minutes, 160 minutes, 165 minutes, 170 minutes, 175 minutes, 180 minutes, 185 minutes, 190 minutes, 195 minutes, 200 minutes, 205 minutes, 210 minutes, 215 minutes, 220 minutes, 225 minutes, 230 minutes, 235 minutes, 245 minutes, 250 minutes, 255 minutes, 260 minutes, 265 minutes, 270 minutes, 275 minutes, 280 minutes, 285 minutes, 290 minutes, 295 minutes, 300 minutes, 305 minutes, 310 minutes, 315 minutes, 320 minutes, 325 minutes, 330 minutes, 335 minutes, 345 minutes, 350 minutes, 355 minutes, 360 minutes, 365 minutes, 370 minutes, 375 minutes, 380 minutes, 385 minutes, 390 minutes, 395 minutes, 400 minutes, 405 minutes, 410 minutes, 415 minutes, 420 minutes, 425 minutes, 430 minutes, 435 minutes, 445 minutes, 450 minutes, 455 minutes, 460 minutes, 465 minutes, 470 minutes, 475 minutes, 480 minutes, 485 minutes, 490 minutes, 495 minutes, or 500 minutes, and the duration may include a medium range of these values. As the reaction time of step (b) is longer, the purity of a product may increase, but when the reaction time is excessively long, the productivity may deteriorate.

Step (b) may react the resulting product, which has been reacted in the first reaction part at a predetermined level, using the second reaction part at a high temperature, thereby improving the overall reaction rate, yield and purity.

The reactions of step (a) and step (b) may be di-nitrilation through a direct substitution reaction of a carboxyl group and a nitrile-based group, and an example thereof may be represented by the following reaction formula:

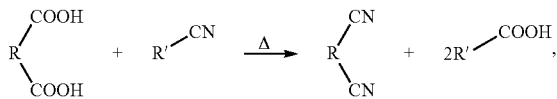

wherein R may be an aromatic ring such as phenylene, and R' may be an alkyl group having 1 to 20 carbon atoms, for example, a methyl group, an ethyl group, an isopropyl group, a t-butyl group, etc.

Step (c) may be a step of performing separation and purification of a phthalonitrile-based compound from a product obtained at the discharge part 300. The separation and purification may separate a phthalonitrile-based compound from a residual compound, and may be performed according to any known methods such as distillation separation. The residual compound may include at least one selected from the group consisting of, for example, a unreacted phthalic acid-based compound, a unreacted nitrile-based compound and a phthalonitrile-based compound in which only part of the carboxyl groups of a phthalic acid-based compound is reacted, but is not limited thereto.

The residual compound, excluding the phthalonitrile-based compound, which is separated in step (c) may be reused in step (a). A method for preparing a phthalonitrile-based compound according to an embodiment of the present specification may be performed without any additive such as a catalyst, and the residual compound may be reused without purification.

According to the method for preparing a phthalonitrile-based compound, a phthalonitrile-based compound, a product, may have a purity of 60% or more, 65% or more, 70% or more, 75% or more, 80% or more, 85% or more, 90% or more, or 95% or more.

Hereinafter, embodiments of the present specification will be described in more detail. However, the following experimental results describe only representative experimental results among the above examples, and the scope and content of the present specification may not be construed as narrowed or limited by the examples. Each effect of the various embodiments of the present specification not explicitly presented below will be specifically described in the corresponding section.

Reactor

First reactor: tank reactor having a stirrer, with a capacity of 100 parts by volume Second reactor: tubular reactor having a length that is 670 times of a square root of a cross-sectional area, with a capacity of 6 parts by volume Example 1

75 g of isophthalic acid (IPA) and 1,500 g of acetonitrile (ACN) were fed into a first reactor having a stirrer. Nitrogen was substituted three times inside the first reactor at a pressure of 2 to 3 bar. The internal temperature of the first reactor was raised to 280° C. while stirring the first reactor at 600 rpm. The reaction was carried out for 1 hour while maintaining the reaction temperature of 280° C. and reaction pressure of 85 to 90 bar, and then the reactant was transferred to a second reactor having the reaction temperature of 350 to 400° C. and reaction pressure of 85 to 90 bar at a flow rate of 1,000 ml/min. After transferring a product obtained at the end of the second reactor to a distillation column, the product was distilled under vacuum to remove acetonitrile and acetic acid. The removed acetonitrile was reused. The remaining product was analyzed using gas chromatography (GPC) to confirm the purity, and by-products were separated through additional purification to obtain isophthalonitrile (IPN).

Example 2

75 to 214.3 g of isophthalic acid and 1,500 g of acetonitrile were fed into a first reactor having a stirrer. Nitrogen was substituted three times inside the first reactor at a pressure of 2 to 3 bar. The internal temperature of the first reactor was raised to 280° C. while stirring the first reactor at 600 rpm. The reaction was carried out for 1 hour while maintaining the reaction temperature of 280° C. and reaction pressure of 85 to 90 bar, and then the reactant was transferred to a second reactor having the reaction temperature of 400° C. and reaction pressure of 85 to 90 bar at a flow rate of 1,000 ml/min. After transferring a product obtained at the end of the second reactor to a distillation column, the product was distilled under vacuum to remove acetonitrile and acetic acid. The removed acetonitrile was reused. The remaining product was analyzed using gas chromatography at 30-minute intervals to confirm the purity, and by-products were separated through additional purification to obtain isophthalonitrile.

Comparative Example 1

150 g of isophthalic acid and 1,500 g of acetonitrile were fed into a first reactor having a stirrer to form a reaction system. Nitrogen was substituted three times inside the first reactor at a pressure of 2 to 3 bar. The internal temperature of the first reactor was raised to 280° C. while stirring the first reactor at 600 rpm. The reaction was carried out for 4 hours while maintaining the reaction temperature of 280° C. and reaction pressure of 85 to 90 bar. After having completed the reaction, the reaction system was cooled down to room temperature. Then, the reaction system was distilled under vacuum to remove acetonitrile and acetic acid. The removed acetonitrile was reused. The remaining product was analyzed using gas chromatography to confirm the purity, and by-products were separated through additional purification to obtain isophthalonitrile.

Comparative Example 2

75 g of isophthalic acid and 1,500 g of acetonitrile were fed into a first reactor having a stirrer. Nitrogen was substituted three times inside the first reactor at a pressure of 2 to 3 bar. The internal temperature of the first reactor was raised to 280° C. while stirring the first reactor at 600 rpm. The reaction was carried out for 1 hour while maintaining the reaction temperature of 280° C. and reaction pressure of 85 to 90 bar, and then the reactant was transferred to a second reactor having the reaction temperature of 280 to 300° C. and reaction pressure of 85 to 90 bar at a flow rate of 1,000 ml/min. After transferring a product obtained at the end of the second reactor to a distillation column, the product was distilled under vacuum to remove acetonitrile and acetic acid. The removed acetonitrile was reused. The remaining product was analyzed using gas chromatography to confirm the purity, and by-products were separated through additional purification to obtain isophthalonitrile.

Comparative Example 3

150 g of isophthalic acid and 1,500 g of acetonitrile were fed into a first reactor having a stirrer. Nitrogen was substituted three times inside the first reactor at a pressure of 2 to 3 bar. The internal temperature of the first reactor was raised to 280° C. while stirring the first reactor at 600 rpm. The reaction was carried out for 1 hour while maintaining the reaction temperature of 280° C. and reaction pressure of 85 to 90 bar, and then the reactant was transferred to a second reactor having the reaction temperature of 280° C. and reaction pressure of 85 to 90 bar at a flow rate of 500 to 1,000 ml/min. After transferring a product obtained at the end of the second reactor to a distillation column, the product was distilled under vacuum to remove acetonitrile and acetic acid. The removed acetonitrile was reused. The remaining product was analyzed using gas chromatography to confirm the purity, and by-products were separated through additional purification to obtain isophthalonitrile.

Comparative Example 4

75 to 214.3 g of isophthalic acid and 1,500 g of acetonitrile were fed into a first reactor having a stirrer. Nitrogen was substituted three times inside the first reactor at a pressure of 2 to 3 bar. The internal temperature of the first reactor was raised to 280° C. while stirring the first reactor at 600 rpm. The reaction was carried out for 1 hour while maintaining the reaction temperature of 280° C. and reaction pressure of 85 to 90 bar, and then the reactant was transferred to a second reactor having the reaction temperature of 280° C. and reaction pressure of 85 to 90 bar at a flow rate of 1,000 ml/min. After transferring a product obtained at the end of the second reactor to a distillation column, the product was distilled under vacuum to remove acetonitrile and acetic acid. The removed acetonitrile was reused. The remaining product was analyzed using gas chromatography to confirm the purity, and by-products were separated through additional purification to obtain isophthalonitrile.

The reaction conditions and gas chromatography analysis results of the examples and comparative examples are as shown in Table 1 below. As a result of gas chromatography analysis, 3-cyanobenzoic acid (3-CBAc), 3-cyanobenzamide (3-CBAm) and N-acetyl-3-cyano-benzamide (3-CBAA) were detected as by-products.

TABLE 1

|  | Amount of reactant fed | | Reaction conditions of second reactor | | | GPC analysis results | | | |
| --- | --- | --- | --- | --- | --- | --- | --- | --- | --- |
|  | IPA (g) | ACN (g) | Reaction temperature (° C.) | Flow rate (ml/min) | Reaction time (hr) | IPN (%) | 3-CBAc (%) | 3-CBAm (%) | 3-CBAA (%) |
| Ex. 1-1 | 75 | 1500 | 350 | 1000 | 2.5 | 82.3 | 15.1 | 2 | 0.5 |
| Ex. 1-2 | 75 | 1500 | 400 | 1000 | 2.5 | 84.7 | 12.8 | 2.1 | 0.3 |
| Ex. 2-1 | 75 | 1500 | 400 | 1000 | 0.5 | 80.3 | 16.6 | 2.5 | 0.6 |
| Ex. 2-2 | 75 | 1500 | 400 | 1000 | 1.0 | 80.8 | 16.3 | 2.4 | 0.5 |
| Ex. 2-3 | 75 | 1500 | 400 | 1000 | 1.5 | 83 | 14.2 | 2.4 | 0.4 |
| Ex. 2-4 | 75 | 1500 | 400 | 1000 | 2.0 | 83.7 | 13.6 | 2.2 | 0.4 |
| Ex. 2-5 | 75 | 1500 | 400 | 1000 | 2.5 | 84.7 | 12.8 | 2.1 | 0.3 |
| Ex. 2-6 | 100 | 1500 | 400 | 1000 | 2.5 | 83.2 | 14.9 | 1.6 | 0.4 |
| Ex. 2-7 | 150 | 1500 | 400 | 1000 | 2.5 | 82 | 16.8 | 0.7 | 0.5 |
| Ex. 2-8 | 214.3 | 1500 | 400 | 1000 | 2.5 | 75.5 | 22.2 | 1 | 0.9 |
| Comp. Ex. 1 | 150 | 1500 | — | — | 4.0 | 67.5 | 24.1 | 2.9 | 5.4 |
| Comp. Ex. 2-1 | 75 | 1500 | 280 | 1000 | 2.5 | 81.8 | 14.8 | 1.8 | 1.5 |
| Comp. Ex. 2-2 | 75 | 1500 | 300 | 1000 | 2.5 | 82 | 15.3 | 2.2 | 1.1 |
| Comp. Ex. 3-1 | 150 | 1500 | 280 | 1000 | 2.5 | 76.9 | 19.5 | 1.1 | 2.4 |
| Comp. Ex. 3-2 | 150 | 1500 | 280 | 700 | 2.5 | 78.2 | 18.3 | 0.9 | 2.6 |
| Comp. Ex. 3-3 | 150 | 1500 | 280 | 500 | 2.5 | 79.1 | 17.3 | 1.7 | 1.7 |
| Comp. Ex. 4-1 | 75 | 1500 | 280 | 1000 | 2.5 | 81.8 | 14.8 | 1.8 | 1.5 |
| Comp. Ex. 4-2 | 100 | 1500 | 280 | 1000 | 2.5 | 81.2 | 15.5 | 1.5 | 1.7 |
| Comp. Ex. 4-3 | 150 | 1500 | 280 | 1000 | 2.5 | 76.9 | 19.5 | 1.1 | 2.4 |
| Comp. Ex. 4-4 | 214.3 | 1500 | 280 | 1000 | 2.5 | 68.5 | 26.2 | 1.7 | 3.4 |

Referring to example 1 and comparative example 2, as the reaction temperature of the second reactor was higher, the purity of the product isophthalonitrile increased.

Referring to example 2-1 to example 2-5, as the reaction time was longer, the purity of the product isophthalonitrile increased.

In addition, referring to example 2-5 to example 2-8 and comparative example 4, as the amount of acetonitrile fed was larger compared to the amount of isophthalic acid fed, the purity of isophthalonitrile increased. It was confirmed that example 2-5, in which the reaction temperature of the second reactor is 400° C., and the amount of acetonitrile fed is 20 parts by weight based on 1 part by weight of isophthalic acid, achieved the highest purity.

It was confirmed that the rate of the by-product 3-CBAA in the examples in which the reaction temperature of the second reactor is 350 to 400° C. was less than 1.0%, and that the rate of 3-CBAA in said examples was lower than that in the comparative examples in which the reaction temperature of the second reactor is 280 to 300° C.

Referring to comparative example 3, as the flow rate of the reactant transferred from the first reactor to the second reactor increased, the purity of isophthalonitrile increased.

Upon comparing comparative example 1 that is a batch process using only the first reactor with comparative example 3 that is a continuous process using the first reactor and second reactor, both of which used the same reactant and reaction temperature, it can be confirmed that the continuous process achieved isophthalonitrile of higher purity than the batch process, even for a shorter reaction time.

Unlike conventional preparing processes using an ammoxidation reaction that uses harmful chemical materials such as ammonia, an acid catalyst, etc., an embodiment of the present specification may prepare a phthalonitrile-based compound with high yield from a phthalic acid-based compound without any catalyst or additive. In addition, an embodiment of the present specification may prepare a product of higher purity for a shorter reaction time than comparative example 1 which performs a batch process reaction using a continuous process, and may prepare isophthalonitrile of high purity by setting the reaction temperature of the second reactor of the continuous process to a high temperature and thereby reducing the rate of the by-product 3-CBAA. This is because 3-CBAA produced at the first reactor was decomposed while being passed through the second reactor of a high temperature, and was converted into isophthalonitrile.

Specifically, the examples used isophthalic acid, a phthalic acid-based compound, as a reactant and acetonitrile, an organic nitrile, as a solvent and also a reactant. The examples formed the reaction conditions of high temperature and high pressure by directly heating the mixture thereof without any catalyst or additive, and induced an exchange reaction of acid and nitrile to directly prepare a phthalonitrile-based compound. In addition, the examples performed the reaction using a tank reactor and a tubular reactor, and set the temperature of the tubular reactor to be high, thereby preparing a product of high purity for a shorter reaction time. As a result, the purification and separation of a final product were performed more easily.

The foregoing description of the present invention has been presented for illustrative purposes, and it is apparent to a person having ordinary skill in the art that the present invention can be easily modified into other detailed forms without changing the technical idea or essential features of the present invention. Therefore, it should be understood that the forgoing embodiments are by way of example only, and are not intended to limit the present disclosure. For example, each component which has been described as a unitary part can be implemented as distributed parts. Likewise, each component which has been described as distributed parts can also be implemented as a combined part.

The scope of the present invention is presented by the accompanying claims, and it should be understood that all changes or modifications derived from the definitions and scopes of the claims and their equivalents fall within the scope of the present invention.

DESCRIPTION OF REFERENCE NUMERALS

100: first reaction part
200: second reaction part
300: discharge part
120, 220, 320: temperature control part
400: pressure control part

What is claimed is:

1. A method for preparing a phthalonitrile-based compound, comprising:
    (a) feeding a mixture comprising a phthalic acid-based compound and a nitrile-based compound into a first reaction part to react;
    (b) transferring a resulting product of step (a) to a second reaction part connected to the first reaction part to react under the condition of 350 to 400° C.; and
    (c) obtaining a phthalonitrile-based compound at a discharge part connected to the second reaction part,
    wherein the second reaction part has a length in a fluid flow direction which is 10 times or more of a square root of an average cross-sectional area perpendicular to the fluid flow direction.

2. The method of claim 1, wherein the second reaction part has a capacity of 1 to 50 parts by volume based on 100 parts by volume of the first reaction part.

3. The method of claim 1, wherein the phthalic acid-based compound is isophthalic acid, terephthalic acid or a mixture thereof.

4. The method of claim 1, wherein the nitrile-based compound is at least one selected from the group consisting of hydrogen cyanide, acetonitrile, acrylonitrile, butyronitrile, isobutyronitrile, pivalonitrile, succinonitrile, fumaronitrile, crotonitrile and benzonitrile.

5. The method of claim 1, wherein in step (a), the nitrile-based compound is contained in an amount of 1 to 500 parts by weight based on 1 part by weight of the phthalic acid-based compound.

6. The method of claim 1, wherein in step (a), the mixture has a water content of less than 6,000 ppm.

7. The method of claim 1, wherein the reaction of step (a) is performed under the conditions of 260 to 350° C. and 40 to 200 bar.

8. The method of claim 1, wherein in step (b), a flow rate of the resulting product of step (a) transferred to the second reaction part is adjusted to 100 to 5,000 ml/min.

9. The method of claim 1, wherein in step (b), the resulting product of step (a) and the second reaction part are in contact for 60 minutes or less.

10. The method of claim 1, wherein the reaction in step (b) is performed under the condition of 40 to 200 bar.

11. The method of claim 1, wherein step (b) is performed for 1 to 500 minutes.

12. The method of claim 1, wherein step (c) performs separation and purification of the phthalonitrile-based compound from a product obtained at the discharge part.

13. The method of claim 12, wherein a residual compound separated in step (c) is reused in step (a).

* * * * *